US007986790B2

(12) United States Patent
Zhang et al.

(10) Patent No.: US 7,986,790 B2
(45) Date of Patent: Jul. 26, 2011

(54) SYSTEM FOR EVALUATING HEARING ASSISTANCE DEVICE SETTINGS USING DETECTED SOUND ENVIRONMENT

(75) Inventors: Tao Zhang, Eden Prairie, MN (US); Jon S. Kindred, Minneapolis, MN (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 1375 days.

(21) Appl. No.: 11/276,795

(22) Filed: Mar. 14, 2006

(65) Prior Publication Data

US 2007/0217620 A1 Sep. 20, 2007

(51) Int. Cl.
*H04R 29/00* (2006.01)
*H04R 25/00* (2006.01)
*A61N 1/00* (2006.01)

(52) U.S. Cl. .......... 381/60; 381/312; 381/314; 381/315; 600/25; 607/56; 607/57

(58) Field of Classification Search .................... 381/60, 381/312; 600/25; 607/56, 57; 707/999.104, 707/999.102, 999.107
See application file for complete search history.

(56) References Cited

U.S. PATENT DOCUMENTS

| | | | |
|---|---|---|---|
| 5,226,086 | A | 7/1993 | Platt |
| 5,687,279 | A | 11/1997 | Matthews |
| 5,706,352 | A | 1/1998 | Engebretson et al. |
| 5,724,433 | A | 3/1998 | Engebretson et al. |
| 6,118,877 | A | 9/2000 | Lindemann et al. |
| 6,718,301 | B1 | 4/2004 | Woods |
| 6,782,361 | B1 | 8/2004 | El-Maleh et al. |
| 6,885,752 | B1 | 4/2005 | Chabries et al. |
| 6,912,289 | B2 | 6/2005 | Vonlanthen et al. |
| 7,006,646 | B1 | 2/2006 | Baechler |
| 7,149,320 | B2 | 12/2006 | Haykin et al. |

(Continued)

FOREIGN PATENT DOCUMENTS

AU 2005100274 A4 6/2005

(Continued)

OTHER PUBLICATIONS

Preves, David A., "Field Trial Evaluations of a Switched Directional/Omnidirectional In-the-Ear Hearing Instrument", *Journal of the American Academy of Audiology*, 10(5), (May 1999), 273-283.

(Continued)

*Primary Examiner* — Curtis Kuntz
*Assistant Examiner* — Sunita Joshi
(74) *Attorney, Agent, or Firm* — Schwegman, Lundberg & Woessner, P.A.

(57) ABSTRACT

The present subject matter provides method and apparatus for hearing assistance devices, and more particularly to a system for evaluating hearing assistance device settings using detected sound environment. Various examples of a hearing assistance device and method using actual use and hypothetical use logs are provided. Such logs provide a dispenser or audiologist the ability to see how a device is operating with actual settings and how the device would have operated had hypothetical settings been used instead. In various examples, the system allows for collection of statistical information about actual and hypothetical use which can assist in parameter setting determinations for a specific user. The settings may be tailored to that user's commonly experienced sound environment. Wireless communications of usage logs is discussed. Additional method and apparatus can be found in the specification and as provided by the attached claims and their equivalents.

20 Claims, 2 Drawing Sheets

U.S. PATENT DOCUMENTS

| | | | |
|---|---|---|---|
| 7,158,931 B2 | 1/2007 | Allegro | |
| 7,242,777 B2 | 7/2007 | Leenen et al. | |
| 7,283,638 B2 | 10/2007 | Troelsen et al. | |
| 7,283,842 B2 | 10/2007 | Berg | |
| 7,349,549 B2 | 3/2008 | Bachler et al. | |
| 7,383,178 B2 | 6/2008 | Visser et al. | |
| 7,454,331 B2 | 11/2008 | Vinton et al. | |
| 2001/0055404 A1 | 12/2001 | Bisgaard | |
| 2002/0191799 A1 | 12/2002 | Nordqvist et al. | |
| 2002/0191804 A1 | 12/2002 | Luo et al. | |
| 2003/0007647 A1 | 1/2003 | Nielsen et al. | |
| 2003/0112988 A1* | 6/2003 | Naylor | |
| 2003/0144838 A1 | 7/2003 | Allegro | |
| 2004/0015352 A1 | 1/2004 | Ramakrishnan et al. | |
| 2004/0066944 A1 | 4/2004 | Leenen et al. | |
| 2004/0190739 A1* | 9/2004 | Bachler et al. | 381/314 |
| 2004/0202340 A1 | 10/2004 | Armstrong et al. | |
| 2005/0069162 A1 | 3/2005 | Haykin et al. | |
| 2005/0111683 A1 | 5/2005 | Chabries et al. | |
| 2005/0129262 A1* | 6/2005 | Dillon et al. | 381/312 |
| 2005/0283263 A1 | 12/2005 | Eaton et al. | |
| 2006/0222194 A1 | 10/2006 | Bramslow et al. | |
| 2006/0227987 A1 | 10/2006 | Hasler | |
| 2007/0009123 A1 | 1/2007 | Aschoff et al. | |
| 2007/0019817 A1 | 1/2007 | Siltmann | |
| 2007/0029300 A1* | 2/2007 | Platz | |
| 2007/0135862 A1 | 6/2007 | Nicolai et al. | |
| 2007/0217629 A1 | 9/2007 | Zhang et al. | |
| 2007/0219784 A1 | 9/2007 | Zhang et al. | |
| 2007/0237346 A1 | 10/2007 | Fichtl et al. | |
| 2007/0276285 A1 | 11/2007 | Burrows et al. | |
| 2007/0299671 A1 | 12/2007 | McLachlan et al. | |
| 2008/0019547 A1 | 1/2008 | Baechler | |
| 2008/0037798 A1* | 2/2008 | Baechler et al. | |
| 2008/0049957 A1 | 2/2008 | Topholm | |
| 2008/0107296 A1 | 5/2008 | Bachler et al. | |
| 2009/0154741 A1 | 6/2009 | Woods et al. | |

FOREIGN PATENT DOCUMENTS

| | | | |
|---|---|---|---|
| AU | 2002224722 B2 | | 4/2008 |
| CA | 2439427 | | 4/2002 |
| EP | 0396831 A2 | | 11/1990 |
| EP | 0335542 B1 | * | 12/1994 |
| EP | 1256258 B1 | | 3/2005 |
| WO | WO-0176321 A1 | | 10/2001 |
| WO | WO-0232208 A2 | | 4/2002 |
| WO | WO-03045108 A2 | * | 5/2003 |
| WO | WO-2005002433 A1 | | 1/2005 |
| WO | WO-2005018275 A2 | * | 2/2005 |
| WO | WO-2007045276 A1 | * | 4/2007 |
| WO | WO-2007112737 A1 | * | 10/2007 |

OTHER PUBLICATIONS

"U.S. Appl. No. 11/276,793, Response filed Nov. 11, 2009 to Non Final Office Action mailed May 12, 2009", 16 pgs.

"U.S. Appl. No. 11/276,793, Non-Final Office Action mailed May 12, 2009", 20 pgs.

"European Search Report for corresponding EP Application No. EP 07250920", (May 3, 2007) ,6 pgs.

"European Application Serial No. 08253924.8, Search Report mailed on Jul. 1, 2009", 8 pgs.*

Mueller, Gustav H, "Data logging: It's popular, but how can this feature be used to help patients?", *The Hearing Journal* vol. 60, No. 10, XP002528491, (Oct. 2007), 6 pgs.*

"U.S. Appl. No. 11/276,793 Final Office Action mailed Aug. 12, 2010", 27 Pgs.

"U.S. Appl. No. 11/276,793, Non Final Office Action mailed Jan. 19, 2010", 22 pgs.

"U.S. Appl. No. 11/276,793, Response filed Jun. 21, 2010 to Non Final Office Action mailed Jan. 19, 2010", 10 pgs.

"U.S. Appl. No. 11/276,793, Response filed Jun. 21, 2010 to Non Final Office Action mailed Jan. 19, 2010", 10 pgs.

"U.S. Appl. No. 11/276,793, Response filed Jun. 21, 2010 to Non Final Office Action mailed Jan. 19, 2010", 10 pgs.

"U.S. Appl. No. 11/276,793 Non-Final Office Action mailed Jan. 19, 2010", 23 Pgs.

"European Application Serial No., 08253924.8, Office Action Mailed Feb. 12, 2010", 1 page.

"European Application Serial No., 08253924.8, Office Action Response Filed Aug. 13, 2010", 14 pgs.

"U.S. Appl. No. 11/276,793, Non Final Office Action mailed Feb. 9, 2011", 25 pgs.

"U.S. Appl. No. 11/276,793, Response filed Jan. 12, 2011 to Final Office Action mailed Aug. 12, 2010", 11 pgs.

"European Application Serial No. 07250920.1, Extended Europen Search Report mailed May 11, 2007", 6 pgs.

El-Maleh, Khaled Helmi, "Classification-Based Techniques for Digital Coding of Speech-plus-Noise", Department of Electrical & Computer Engineering, McGill University, Montreal, Canada, A thesis submitted to McGill University in partial fulfillment of the requirements for the degree of Doctor of Philosophy., (Jan. 2004), 152 pgs.

* cited by examiner

SYSTEM FOR EVALUATING HEARING ASSISTANCE DEVICE SETTINGS USING DETECTED SOUND ENVIRONMENT

TECHNICAL FIELD

This disclosure relates to hearing assistance devices, and more particularly to a system for evaluating hearing assistance device settings using detected sound environment.

BACKGROUND

When a user of a hearing assistance device, such as a hearing aid, gets a new device, the dispenser or audiologist can make some educated guesses as to settings based on the user's hearing. Improvements to the settings are possible if the sound environment commonly experienced by the user is known. However, such information takes time to acquire and is not generally immediately known about the user. Different users may be exposed to very different sound environments, and settings may be changed for better performance.

Some attempts at logging sound environments have been done which can enhance the ability of a dispenser or audiologist to improve device settings. However, advanced, highly programmable hearing assistance devices may provide a number of modes which can provide unpredictable performance depending on the particular hearing assistance device and the environment the device is exposed to.

What is needed in the art is an improved system for assisting hearing device parameter selection based on the sound environment commonly experienced by a particular user. The system should be straightforward for a dispenser or audiologist to use and should provide support for setting decisions in advanced, highly programmable devices.

SUMMARY

The above-mentioned problems and others not expressly discussed herein are addressed by the present subject matter and will be understood by reading and studying this specification.

The present subject matter provides method and apparatus for hearing assistance devices, and more particularly to a system for evaluating hearing assistance device settings using detected sound environment. Various examples of a hearing assistance device and method using actual use and hypothetical use logs are provided. Such logs provide a dispenser or audiologist the ability to see how a device is operating with actual settings and how the device would have operated had hypothetical settings been used instead. In various examples, the system allows for collection of statistical information about actual and hypothetical use which can assist in parameter setting determinations for a specific user. The settings may be tailored to that user's commonly experienced sound environment.

Additional examples of multiple hypothetical usage logs are provided.

Methods and apparatus of programming hearing assistance devices, accessing the data from the logs, presenting the data, and using the data are provided. Various applications in hearing aids are described.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their legal equivalents.

DETAILED DESCRIPTION

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in a limiting sense. The scope of the present subject matter is defined by the appended claims, along with the full scope of legal equivalents to which such claims are entitled.

The present subject matter relates to methods and apparatus for hearing assistance devices, and more particularly to a system for evaluating hearing assistance device settings using detected sound environment. The method and apparatus set forth herein are demonstrative of the principles of the invention, and it is understood that other method and apparatus are possible using the principles described herein.

Figure 1:
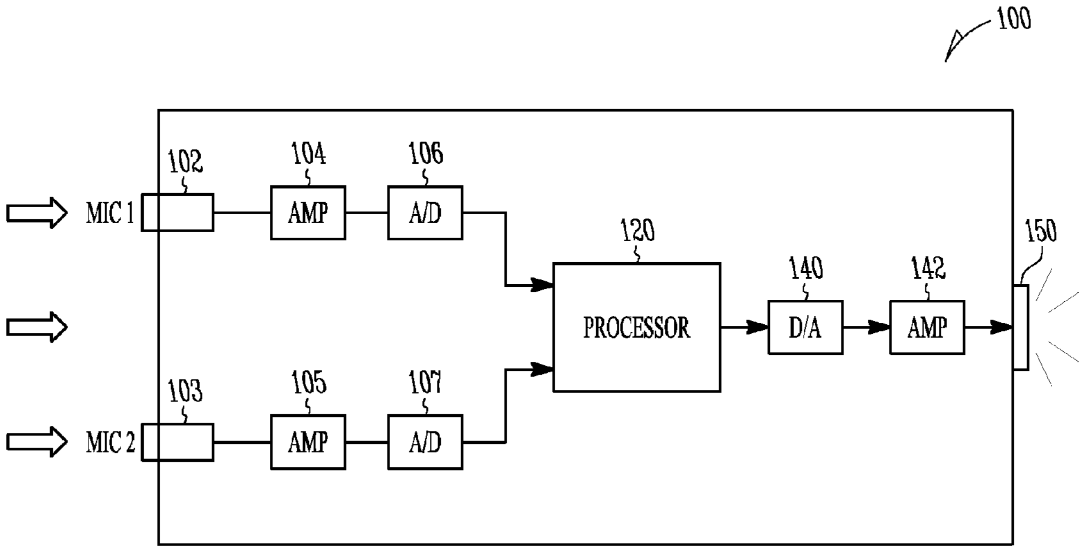
FIG. 1 shows a block diagram of a hearing assistance device, according to one embodiment of the present subject matter.

FIG. 1 shows a block diagram of a hearing assistance device, according to one embodiment of the present subject matter. In one embodiment, hearing assistance device 100 is a hearing aid. In one embodiment, mic 1 102 is an omnidirectional microphone connected to amplifier 104 which provides signals to analog-to-digital converter 106 ("A/D converter"). The sampled signals are sent to processor 120 which processes the digital samples and provides them to the digital-to-analog converter 140 ("D/A converter"). Once the signals are analog, they can be amplified by amplifier 142 and audio sound can be played by receiver 150 (also known as a speaker). Although FIG. 1 shows D/A converter 140 and amplifier 142 and receiver 150, it is understood that other outputs of the digital information may be provided. For instance, in one embodiment, the digital data is sent to another device configured to receive it. For example, the data may be sent as streaming packets to another device which is compatible with packetized communications. In one embodiment, the digital output is transmitted via digital radio transmissions. In one embodiment, the digital radio transmissions are packetized and adapted to be compatible with a standard. Thus, the present subject matter is demonstrated, but not intended to be limited, by the arrangement of FIG. 1.

In one embodiment, mic 2 103 is a directional microphone connected to amplifier 105 which provides signals to analog-to-digital converter 107 ("A/D converter"). The samples from A/D converter 107 are received by processor 120 for processing. In one embodiment, mic 2 103 is another omnidirectional microphone. In such embodiments, directionality is controllable via phasing mic 1 and mic 2. In one embodiment, mic 1 is a directional microphone with an omnidirectional setting. In one embodiment, the gain on mic 2 is reduced so that the system 100 is effectively a single microphone system. In one embodiment, (not shown) system 100 only has one microphone. Other variations are possible which are within the principles set forth herein.

Processor 120 includes modules for execution that will detect environments and make adaptations accordingly as set forth herein. Such processing can be on one or more audio inputs, depending on the function. Thus, even though, FIG. 1 shows two microphones, it is understood that many of the teachings herein can be performed with audio from a single microphone. It is also understood that audio transducers other than microphones can be used in some embodiments.

Figure 2:
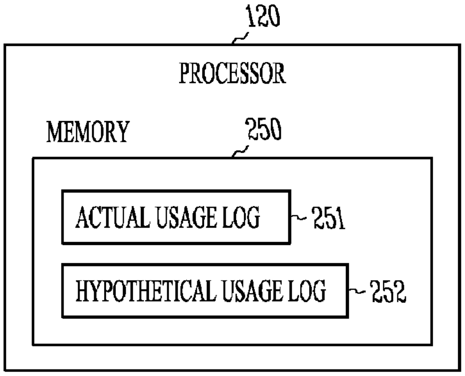
FIG. 2 shows a block diagram of demonstrating storage in the processor of FIG. 1, according to one embodiment of the present subject matter.
Figure 3:
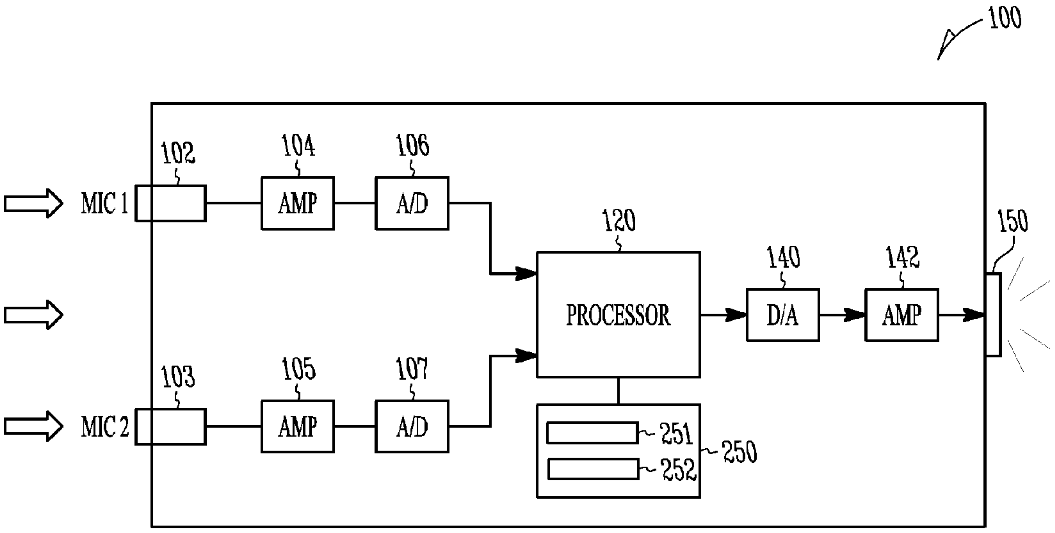
FIG. 3 shows a block diagram of a hearing assistance device, according to one embodiment of the present subject matter.
Figure 4:
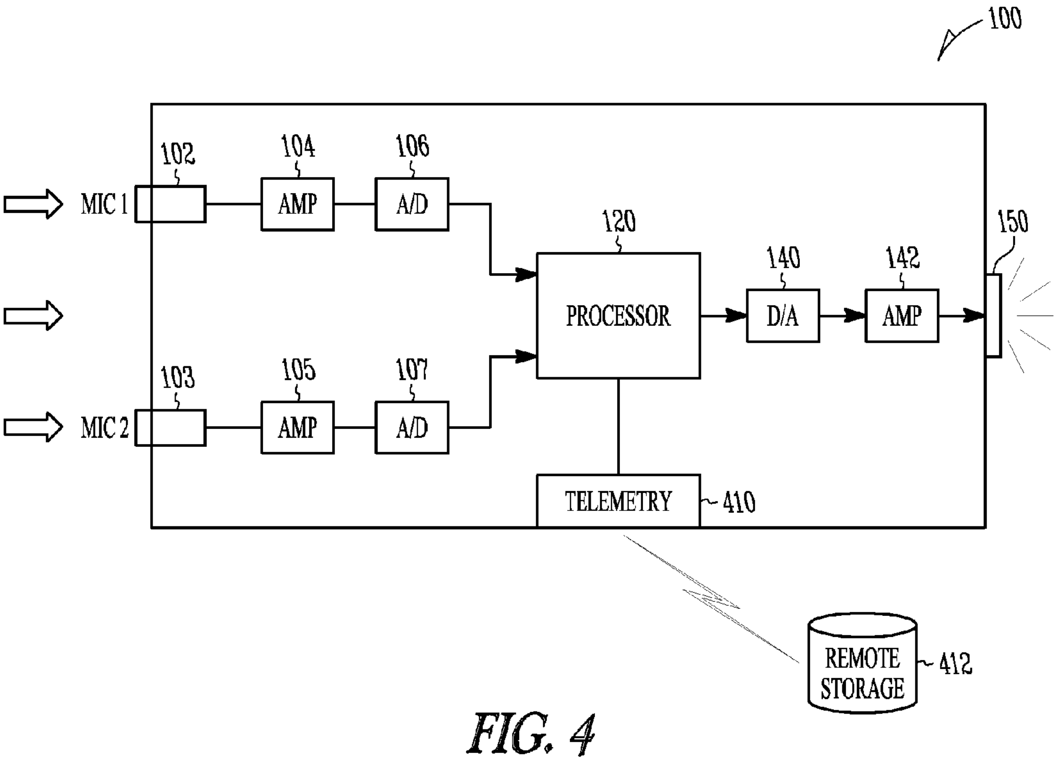
FIG. 4 shows a block diagram of a hearing assistance device, according to one embodiment of the present subject matter.

FIG. 2 shows a block diagram of demonstrating storage in the processor of FIG. 1, according to one embodiment of the present subject matter. Processor 120 is adapted for access to memory 250. It is understood that in various embodiments the memory 250 is physically included in processor 120. In some embodiments, as demonstrated by FIG. 3, memory 250 is accessible by processor 120, but on a separate chip. In some embodiments, as demonstrated by FIG. 4, memory 250 can exist in forms that are resident in the device 100 and forms that are transmitted to another device 412 for storage. In this embodiment, telemetry interface 410 is capable of sending data wirelessly to the remote storage 412. Protocols for wireless transmissions include, but are not limited to, standard or nonstandard communications. Some examples of standard wireless communications include link protocols including, but not limited to, Bluetooth™, IEEE 802.11 (wireless LANs), 802.15 (WPANs), 802.16 (WiMAX), 802.20, cellular protocols including, but not limited to CDMA and GSM, ZigBee, and ultra-wideband (UWB) technologies. Such protocols support radio frequency communications and some support infrared communications. It is possible that other forms of wireless communications can be used such as ultrasonic, optical, and others. It is understood that the standards which can be used include past and present standards. It is also contemplated that future versions of these standards and new future standards may be employed without departing from the scope of the present subject matter.

The use of standard communications makes interface 410 readily adapted for use with existing devices and networks, however, it is understood that in some embodiments non-standard communications can also be used without departing from the scope of the present subject matter. Wired interfaces are also available in various embodiments. Thus, various embodiments of storage are contemplated herein, and those provided here are not intended to be exclusive or limiting.

In various embodiments, memory 250 includes an actual usage log 251 and a hypothetical usage log 252. In various embodiments, the actual usage log 251 is a running storage of the modes that device 100 operates in. In some embodiments, actual usage log 251 includes statistical environmental data stored during use. Hypothetical storage log 252 is used to track the modes which device 100 would have entered had those modes been activated during setup of the device. In some embodiments, hypothetical usage log 252 includes statistical environmental data device 100 would have stored. Some examples of modes which the hypothetical storage log 252 can be applied to include, but are not limited to, directionality modes, environmental modes, gain adjustment modes, power conservation modes, telecoils modes and direction audio input modes. The system 100 has storage for actual use parameters and a separate storage for hypothetical usage parameters. In various embodiments, a plurality of hypothetical use logs can be tracked with the device, so that a plurality of hypothetical parameter settings can be programmed and the hypothetical performance of each setting can be predicted. Such comparison can be done between hypothetical usages and between one or more hypothetical usage and the actual usage.

For example, U.S. Provisional Application Ser. No. 60/743,481, filed even date herewith, which is hereby incorporated by reference in its entirety, provides a system for switching between directional and omnidirectional modes of operation. The actual usage log 251 can track when mode changes for enable modes and how frequently such mode changes occur. The hypothetical usage log 252 can track when modes would have changed had they been enabled, and how frequently such mode changes would have occurred. For example, suppose the device settings restrict operation to omnidirectional mode. The actual hypothetical usage log can track how many times the device would have changed to a directional mode, based on the current settings of the device, had that mode been enabled. The actual and hypothetical usage logs show the dispenser or audiologist an example of how settings can be adjusted to improve the device operation. A comparison between the actual and hypothetical usage logs allows a dispenser or audiologist to recommend device settings for a particular user based on his or her typical environment.

In various embodiments, it is possible to change parameters based on the actual and hypothetical use and compare the resulting data logs to see adjust parameter settings for improved operation.

Another example of use is in U.S. application Ser. No. 11,276,793, filed even date herewith, which is hereby incorporated by reference in its entirety, provides a system for environment detection and adaptation. The actual usage log 251 can track when mode changes for enable modes and how frequently such mode changes occur. The hypothetical usage log 252 can track when modes would have changed had they been enabled, and how frequently such mode changes would have occurred. A comparison between the actual and hypothetical usage logs allows a dispenser or audiologist to recommend proper enablement of modes for a user based on his or her typical environment. In this example, the actual usage log can track the number of times the device detected wind noise, machinery noise, one's own speech sound, and other speech sound. The hypothetical usage log can track the number of times the device would have detected wind noise, machinery noise, one's own speech sound, and other speech sound, given the hypothetical detection settings.

The resulting actual and hypothetical usage logs can also be used to determine statistics on the modes based on actual and hypothetical settings. For example, the gain reduction data for wind noise, machinery noise, one's own speech sound, and other speech sound can be averaged to determine actual average gain reduction per source class and hypothetical average gain reduction per source class. The audiologist can adjust the size of gain reduction for each sound class based on the patient's feedback and the actual and hypothetical average gain reduction log. These examples are just some of the possible available statistics that may be used with the actual and hypothetical usage logs.

A variety of other information may be stored in the usage logs. For example, a time stamp and/or date stamp may be employed to put a time and/or date on recorded events. Furthermore, some embodiments store statistics of actual hearing inputs where appropriate to assist an audiologist or dispenser in diagnosing problems or other actions by the device. For example, it is possible to capture and store input sound level histogram. It is also possible to store the feedback canceller statistics when the device signals an entrainment. Such data are limited only by available storage on the hearing assistance device, which is substantial in some embodiments.

It is understood that the usage logs may be accessed using a hearing assistance device programmer. Such programming may be done wired or wirelessly. The usage and hypothetical parameters may also be programmed into the hearing assistance device using the device programmer. Such programmers for applications involve hearing aids are available for a variety of programming options.

The output of the actual usage log and hypothetical usage log (or plurality of hypothetical usage logs in embodiments employing more than one hypothetical usage log) may be depicted in a graphical format to a user and may be displayed by the programmer to review behavior of the hearing assistance device. In embodiments recording environmental aspects, such outputs may be made on a graphical device to monitor behavior, for example, as a function of time and/or frequency. Other forms of output, such as tabular output, are provided in various embodiments. The presentation methods set forth herein are demonstrative and not intended to be exhaustive or exclusive.

The outputs could be of many forms, including, a table such as follows:

TABLE 1

EXAMPLE OF OUTPUTS OF DEVICE USING ACTUAL AND HYPOTHETICAL LOGS

| USAGE | OMNI MODE | DIRECTIONAL MODE |
|---|---|---|
| ACTUAL USAGE | 29% | 71% |
| HYPOTHETICAL USAGE | 15% | 85% |

TABLE 2

EXAMPLE OF OUTPUTS OF DEVICE USING ACTUAL AND HYPOTHETICAL LOGS

| USAGE | WIND | MACHINE | OWN SPEECH | OTHER |
|---|---|---|---|---|
| ACTUAL % | 5% | 10% | 40% | 45% |
| Avg. Gain Reduction | −7 dB | −15 dB | −10 dB | −20 dB |
| HYPOTHETICAL % | 10% | 20% | 25% | 45% |
| Avg. Gain Reduction | −9 dB | −10 dB | −20 dB | −20 dB |

Table 1 shows that the actual usage parameters favor omnidirectional mode than the hypothetical usage parameters. Table 2 shows differences in source classifications based on parameters. Also shown is an average gain reduction which is compiled as a statistic based on a time period of interest. These examples merely demonstrate the flexibility and programmability of the present subject matter and are not intended to be exhaustive or exclusive of the functions supported by the present system.

In one embodiment, the processor of the hearing assistance device can perform statistical operations on data from the actual and hypothetical usage logs. It is understood that data from the usage logs may be processed by software executing on a computer to provide statistical analysis of the data. Also, advanced software solutions can suggest parameters for the dispenser/audiologist based on the actual usage log and one or more hypothetical usage logs.

It is further understood that the principles set forth herein can be applied to a variety of hearing assistance devices, including, but not limited to occluding and non-occluding applications. Some types of hearing assistance devices which may benefit from the principles set forth herein include, but are not limited to, behind-the-ear devices, on-the-ear devices, and in-the-ear devices, such as in-the-canal and/or completely-in-the-canal hearing assistance devices. Other applications beyond those listed herein are contemplated as well.

CONCLUSION

This application is intended to cover adaptations or variations of the present subject matter. It is to be understood that the above description is intended to be illustrative, and not restrictive. Thus, the scope of the present subject matter is determined by the appended claims and their legal equivalents.

What is claimed is:

1. A hearing assistance apparatus, comprising:

a sound sensor to receive acoustic signals and convert them into electrical signals;

a processor connected to process the electrical signals for hearing assistance;

an actual parameter storage for actual parameters;

a hypothetical parameter storage for hypothetical parameters;

a first storage for an actual usage log adapted to log processing of the electrical signals using the actual parameters; and a second storage for a hypothetical usage log adapted to log processing of the electrical signals using the hypothetical parameters, wherein the processor is adapted to update the actual usage log using the actual usage parameters and to update the hypothetical usage log using the hypothetical storage parameters.

2. The apparatus of claim 1, comprising:

an analog-to-digital (A/D) converter connected to convert analog sound signals received by the sound sensor into time domain digital data for processing by the processor.

3. The apparatus of claim 1, comprising:

a digital-to-analog (D/A) converter connected to receive processed digital data from the processor and convert it to output analog signals.

4. The apparatus of claim 3, comprising:

a receiver to convert the output analog signals to sound.

5. The apparatus of claim 1, comprising:

a second hypothetical parameter storage for storing a second set of hypothetical parameters.

6. The apparatus of claim 5, comprising:

a third storage for a second hypothetical usage log, and wherein the processor is adapted to update the second hypothetical usage log using the hypothetical storage parameters.

7. The apparatus of claim 1, wherein the sound sensor includes a first microphone and further comprising a second microphone, the processor adapted for determining omnidirectional and directional modes of operation based on the actual usage parameters and adapted for updating the actual usage log, the processor further adapted for updating the hypothetical usage log based on the hypothetical usage parameters.

8. The apparatus of claim 1, wherein the sound sensor is a microphone and the processor is a digital signal processor adapted for hearing aid processing.

9. The apparatus of claim 8, wherein the digital signal processor includes the actual parameter storage, the hypothetical parameter storage, the first storage, and the second storage.

10. The apparatus of claim 9, further comprising a third storage for a second hypothetical usage log, and wherein the processor is adapted to update the second hypothetical usage log using the hypothetical storage parameters.

11. A hearing assistance apparatus, comprising:

a hearing assistance processor;

a microphone for receiving sounds and converting them into electrical signals for the hearing aid processor;

actual usage log means for recording parameters of the sounds by the processor using one or more actual usage parameters; and hypothetical usage log means for recording parameters of the sounds by the processor using one or more hypothetical usage parameters.

12. The apparatus of claim 11, comprising a receiver for producing acoustic energy based on signals processed by the hearing assistance processor.

13. The apparatus of claim 11, comprising wireless interface means for transmitting actual usage.

14. The apparatus of claim 13, wherein hypothetical usage is transmitted by the wireless interface means.

15. The apparatus of claim 1, comprising:

an analog-to-digital (A/D) converter connected to convert analog sound signals received by the sound sensor into time domain digital data for processing by the processor;

a digital-to-analog (D/A) converter connected to receive processed digital data from the processor and convert it to output analog signals; and a receiver to convert the output analog signals to sound, wherein the sound sensor includes at least one microphone and the processor is a digital signal processor.

16. The apparatus of claim 15, further comprising a telemetry interface configured to send data wirelessly to a remote storage.

17. The apparatus of claim 16, wherein the telemetry interface is configured for wireless communications according to a BLUETOOTH protocol.

18. The apparatus of claim 16, wherein the telemetry interface is configured for wireless communications according to a wireless network protocol, such as IEEE 802.11, IEEE 802.15, or IEEE 802.16.

19. The apparatus of claim 16, wherein the telemetry interface is configured for cellular communications.

20. The apparatus of claim 16, wherein the telemetry interface is configured for packetized communications.

* * * * *